United States Patent [19]
Jeffers et al.

[11] Patent Number: 5,279,745
[45] Date of Patent: Jan. 18, 1994

[54] POLYMER BEADS CONTAINING AN IMMOBILIZED EXTRACTANT FOR SORBING METALS FROM SOLUTION

[75] Inventors: Thomas H. Jeffers; Don C. Seidel, both of Salt Lake City, Utah

[73] Assignee: The United States of America as represented by the Secretary of the Interior, Washington, D.C.

[21] Appl. No.: 818,427

[22] Filed: Dec. 26, 1991

Related U.S. Application Data

[63] Continuation of Ser. No. 429,236, Oct. 18, 1989, Abandoned

[51] Int. Cl.$^5$ .............. C02F 1/42; C12N 11/12; C12N 11/04; B01J 13/02
[52] U.S. Cl. .................. 210/688; 210/681; 427/213.3; 435/179; 435/182; 435/262.5; 435/803
[58] Field of Search .......... 435/174, 177, 178, 179, 435/180, 182, 262.5, 803; 423/1, 6, 22, 24, 54, 70; 210/660, 681, 684, 688; 427/213.3

[56] References Cited

U.S. PATENT DOCUMENTS

| | | | |
|---|---|---|---|
| 3,725,291 | 4/1973 | Serbus et al. | 252/180 |
| 3,909,468 | 9/1975 | Tanaka et al. | 260/8 |
| 3,914,183 | 10/1975 | Johannson et al. | 252/184 |
| 3,929,319 | 1/1976 | Clendinning et al. | 260/7.5 |
| 3,960,771 | 6/1976 | Tanaka et al. | 252/446 |
| 4,021,368 | 5/1977 | Nemec | 252/427 |
| 4,067,821 | 1/1978 | Votapek | 252/427 |
| 4,070,300 | 1/1978 | Moroni et al. | 252/190 |
| 4,133,755 | 1/1979 | Tarao et al. | 210/38 |
| 4,143,201 | 3/1979 | Miyashiro et al. | 428/403 |
| 4,165,302 | 8/1979 | Armenti et al. | 260/8 |
| 4,202,803 | 5/1980 | Signoretto | 260/17.4 |
| 4,203,876 | 5/1980 | Dereppe et al. | 260/17.4 |
| 4,279,790 | 7/1981 | Nakajima et al. | 260/17.4 |
| 4,293,333 | 10/1981 | Drobot | 423/24 |
| 4,293,334 | 10/1981 | Drobot et al. | 423/22 |
| 4,352,883 | 10/1982 | Lim | 435/178 |
| 4,427,775 | 1/1984 | Chen et al. | 435/179 X |
| 4,477,655 | 10/1984 | Holmes | 528/361 |
| 4,528,167 | 7/1985 | Preston | 423/139 |
| 4,563,425 | 1/1986 | Yoshioka et al. | 435/179 X |
| 4,576,969 | 3/1986 | Echigo et al. | 521/28 |
| 4,665,050 | 5/1987 | Degen et al. | 502/402 |
| 4,690,894 | 9/1987 | Brierley et al. | 435/255 X |
| 4,702,838 | 10/1987 | Babcock et al. | 210/638 |
| 4,719,242 | 1/1988 | Yates et al. | 521/28 |
| 4,755,322 | 7/1988 | Narbutt et al. | 252/184 |
| 4,772,430 | 9/1988 | Sauda et al. | 252/628 |
| 4,780,239 | 10/1988 | Snyder et al. | 252/184 |
| 4,818,598 | 4/1989 | Wong | 428/284 |
| 4,822,826 | 4/1989 | Pommier et al. | 528/84.1 |
| 4,876,287 | 10/1989 | Babcock et al. | 524/417 X |
| 4,879,340 | 11/1989 | Moriguchi et al. | 525/54.2 |
| 4,883,596 | 11/1989 | Agui et al. | 210/638 |

OTHER PUBLICATIONS

Nakajima, et al., Eur. J. Appl. Microbiol., vol. 16, 1982, pp. 88–91.

*Primary Examiner*—David M. Naff
*Attorney, Agent, or Firm*—E. Philip Koltos

[57] ABSTRACT

Polymer beads are prepared containing an immobilized extractant for sorbing metal contaminants at concentrations of less than 1 mg/L in dilute aqueous solutions. A preferred polymer is polysulfone and the extractant can be a biomass material or a synthetic chemical compound sorbed into activated carbon. The polymer beads are prepared by dissolving the polymer in an organic solvent to form a solution, adding the extractant to the solution to form a mixture and injecting the mixture through a nozzle into water to form the beads.

12 Claims, 1 Drawing Sheet

POLYMER BEADS CONTAINING AN IMMOBILIZED EXTRACTANT FOR SORBING METALS FROM SOLUTION

This application is a continuation of application Ser. No. 07/429,236 filed Oct. 18, 1989, now abandoned.

FIELD OF THE INVENTION

The present invention relates to the preparation of beads containing immobilized extractants of either biomass material, organic solvents or mixtures of biomass material and organic solvent materials. These beads are used to effectively remove metal contaminants present in low concentrations from dilute solutions, such as processing streams and waste waters. Removal of the metal values from these extractants is accomplished by using dilute mineral acids or other dilute solutions to solubilize the metal.

BACKGROUND OF THE INVENTION

The removal of metal contaminants from aqueous wastes is an important environmental issue, and although the problem of removing toxic and heavy metals from waters has been addressed for many years, few effective treatment options are available that are not reagent and energy requirement intensive, and where the metal values are recoverable in solutions amenable to being further concentrated, without the generation of hazardous sludges or other harmful waste products.

For example, conventional toxic metal recovery technologies have been inefficient when applied to solutions having metal concentrations ranging from less than 1 mg/L to about 100 mg/L.

In the chemical area of toxic metal recovery from dilute aqueous streams, the techniques of recovery have most commonly been by chemical precipitation, ion exchange, reverse osmosis, electrodialysis, solvent extraction (liquid ion exchange), and chemical reduction (Rich, G., and K. Cherry. Hazardous Waste Treatment Technologies. Pudvan Publishing Co., 1987, 169 pp.); however, these procedures are characterized by the disadvantages of incomplete metal removal, high reagent and energy requirements, and generation of toxic sludge or other waste products that must be disposed of, and these disadvantages are particularly conspicuous at the low metal concentrations often encountered in waste waters, where federally-mandated cleanup standards dictate that effluents discharged to public waters contain <1 mg/L of metals such as arsenic, cadmium, lead, mercury, iron and manganese.

On the other hand, although living microbial populations have shown some promise in extracting metals from these solutions (Jennett, J. C., J. E. Smith, and J. M. Hassett. Factors Influencing Metal Accumulation by Algae, NTIS PB83-149377, 124 pp.), (Ngo, V., and W. Poole, Boosting Treatment Pond Performance. Pollution Eng., v. 19, No. 9, Sept 1987, pp. 62-63), Burton, M. A. S., and P. J. Peterson. Metal Accumulation by Aquatic Bryophytes From Polluted Mine Streams. Environ. Pollution, v. 19, No. 1, May 1979, pp. 39-46) and (Tsezos, M., The Selective Extraction of Metals From Solution by Microorganisms: A Brief Overview. Can. Metall. Q., v. 24, No. 2, June 1985, pp. 141-144), it has been found that the maintenance of a healthy microbial population is often difficult owing to the toxicity of the aqueous streams processed, and recovery of the metal-laden microorganisms from solution is also troublesome due to liquid-solid separation problems.

Colonization of polymeric and foam supports with living microorganisms have also received attention, but problems such as nutrient requirements, toxic shock, and recovery of metal values from these supports still exist (Frenay, J. et al. Microbial Recovery of Metals From Low-Grade Materials. Paper and Recycle and Secondary Recovery of Metals, ed. by P. R. Taylor, H. V. Sohn, and N. Jarrett. Pub. by The Metall. Soc., Inc., 1985, pp. 275-278).

It has been found that, immobilization of thermally-killed biomass in a granular or gel matrix (Brierley, J. A. et al. Treatment of Microorganisms With Alkaline Solution to Enhance Metal Uptake Properties. U.S. Pat. No. 4,690,894) and (Nakajima, A., T. Horidoshi, and T. Sakaguchi. Studies on the Accumulation of Heavy Metal Elements in Biological Systems. XXI. Recovery of Uranium by Immobilized Microorganisms. Eur. J. Appl. Microbiol. and Biotechnol., v. 16(2-3), 1982, pp. 88-91) eliminates the need to supply nutrients and the problem of toxic shock, however, these materials are subject to fracture and attrition after repeated loading-elution cycles, especially in acidic solutions. As the granules and gels physically deteriorate, maintenance of aqueous flows in downflow columns is difficult since the fine particles impede the flow. Additionally, recovery of metal values from the metal-laden granules is often difficult.

Solvent extraction has also shown promise for extracting metal values from dilute aqueous solutions, but solubility and entrainment losses of the organic reagents in the aqueous phase result in high reagent costs and contaminate the metal-free aqueous stream with organic compounds.

Attempts have also been made to immobilize solvent extraction reagents in polymeric substrates such as membranes (Nichols, L. D., A. S. Obermayer, and M. B. Allen. Bound Liquid Ion Exchange Membranes For Recovery of Chromium From Wastewater. NTIS PB82-250580, 1980, 33 pp.), and although losses of organic reagent were lower than those encountered with conventional liquid-liquid solvent extraction, the organic reagents slowly desorbed from the beads into the aqueous processing solutions. Also, organic-aqueous complexes frequently precipitated within the substrate pores and plugged the membranes.

Accordingly, there is a need for new and innovative technologies in the mineral processing industry to recover toxic metal values from the low-grade aqueous solutions encountered.

SUMMARY OF THE INVENTION

The Invention innovation over the conventional processes of recovering toxic metal values from low-grade waste waters and aqueous processing solutions is to immobilize various biomass materials and/or chemical substances having natural extractive properties in porous, insoluble, spherical bead mixtures and use these matrices as metal extractants upon bringing them in contact with waste water.

Fabrication of the beads containing immobilized extractants is accomplished by: (1) dissolving high-density polysufone in an organic solvent, such as dimethylformamide (DMF); (2) blending the desired biomass or chemical extractants into the polysulfone-DMF; if desired, (3) blending inert metal powders into the mixture to increase bead density or impart magnetic qualities;

and (4) injecting the mixture through a nozzle into water to form spherical beads.

After the beads are cured by agitation in water, the beads are contacted in a stirred reactor containing toxic metal contaminated water, whereupon the metal is sorbed upon the beads.

DETAIL DESCRIPTION OF THE INVENTION

Figure 1:
FIG. 1 is a cross-sectional photograph (24X magnification) showing the internal pore structure of a polysulfone bead containing immobilized algae (dark matter occupying several of the pores).

It is well known that various biomass materials such as those produced by algae, yeast, bacteria and aquatic flora and commercially produced solvent extraction reagents such as amines, oximes and organo phosphates have the capacity to extract and accumulate metal ions from dilute aqueous solutions. Further, the extraction mechanism is reversible, and the metal ions can be desorbed or eluted from these extractive materials, thereby allowing the extractants to be regenerated and used for metal sorption, wherein the metal values can be recovered as salable products.

However, the utility and uniqueness of the present invention is the immobilization of the extractants in porous, insoluble, spherical beads. The beads are prepared from readily available polymeric materials and can accomodate a wide range of biomass and chemical extractants. Moreover, two or more extractants can be immobilized in the same bead matrix in order to provide flexibility when complex solutions containing different metal valves are processed. It is also of significance that the beads exhibit excellent handling characteristics in existing waste water and hydrometallurgical processing equipment, are stable in strong acid and base solutions, can be utilized in turbid solutions, and can be used for repeated extraction-elution cycles without any decrease in chemical or physical stability.

Generally speaking, preparation of the beads containing immobilizing extractants consists of the following steps: (1) high-density polysulfone is dissolved in an organic solvent such as dimethylformamide (DMF); (2) the desired biomass or chemical extractants are blended into the polysulfone-DMF (the chemical extractants may first be sorbed on powdered activated carbon to aid in their retention within the finished bead); (3) if desired, inert metal powders are blended into the mixture to increase bead density or impart magnetic qualities; and (4) the mixture is injected through a nozzle into water. Spherical beads ranging in size from about 1/16 to about ¼ inch in diameter are immediately formed. The beads are then cured by agitation in water for 16 to 24 hours. The size of the beads can be controlled by selecting the proper injection nozzle size. The resulting beads have a well-developed internal pore structure, and microscopic analysis reveals that the biomass and chemical extractants are immobilized within these pores. A cross-sectional photograph (24× magnification) of a cured bead illustrating the intricate internal pore structure is shown in FIG. 1, wherein the dark matter occupying several of the pores is immobilized algae.

The bead density can be controlled by varying the amount of polysulfone, extractant, or metal powder added during the fabrication process, and beads with a density less than that of water, as well as heavy beads which sink rapidly in aqueous solutions can be produced. Beads are fabricated from mixtures containing 75 to 200 g of polysulfone per liter of organic solvent and the solvent can be dimethylformamide, dimethyl sulfoxide, tetrahydrofuran, acetone or mixtures thereof. Beads containing from 10 to 68 percent of the desired extractant (dry weight basis) are prepared. Specific biomasses immobilized in the beads include biomass produced by yeast, several species of algae, penicillium mold, xanthan gum, alginates, and common duckweed (Lemna sp.).

Specific chemical extractants immobilized include solvent extraction reagents such as triisooctyl amine, di-2-ethylhexyl phosphoric acid, Aliquat 336 (Tri-octyl methylammonium chloride), Lix 64N (2-hydroxy-5-dodecylbenzophenone oxime), and Cyanex 272 (Di-2,4,4-trimethylpentyl phosphoric acid).

The examples hereinafter set forth will illustrate more detailed descriptions of the invention.

EXAMPLE 1

Polysulfone beads were prepared, as described above by dissolving 100 g of high-density polysulfone in a liter of DMF. Fifty nine (59)g. of common duckweed (Lemna sp.) material was thermally-killed and ground with a mortar and pestle to minus 35 plus 60 mesh. The duckweed was blended into the polysulfone-DMF, and the mixture was injected into 25° C. water. After curing, 50 mL of beads were contacted in a stirred reactor with 50 mL of cadmium-contaminated groundwater obtained from the vicinity of a lead smelter. The aqueous-to-biomass (A:B) ratio was 17:1, i.e., 17 mL of waste water per gram of immobilized biomass. The pH 6.4 contaminated groundwater contained 0.018 mg/L of cadmium. Extraction of cadmium by the beads was rapid. In 5 minutes, 62.8 percent of the cadmium was sorbed, and in 60 minutes, 83.3 percent of the cadmium was sorbed. After 60 minutes, the groundwater contained only 0.003 mg/L Cd.

This demonstrates that the Lemna sp.-polysulfone beads readily removed cadmium, which is a common metal contaminant, from very dilute waste waters.

EXAMPLE 2

Two sets of beads were prepared as described above and in Example 1. One set of beads contained 100 g of alginate, (a carbohydrate polymer), and 150 g of polysulfone per liter of DMF. The second set contained a combination of 100 g of xanthan gum and 100 g of guar gum (bacterially produced polysaccharide) in a similar polysulfone matrix. Each set of beads was equilibrated in an ion exchange column with a pH 13, cyanide-leach bleed stream from a gold operation. The bleed stream contained 5.0 mg/L Hg and was continually pumped through the beads until a steady state was reached. In 24 hours at a flow rate of 10.2 bed volumes/hour (BV/h), the alginate polysulfone beads sorbed 98.6 percent of the mercury from 20 BV of the bleed stream. Likewise, the xanthan/guar gum beads removed 96 percent of the mercury from 20 BV of the bleed stream in 24 hours. These tests demonstrate the potential of the beads for removing highly-toxic mercury from mineral processing waste streams.

EXAMPLE 3

Polysulfone beads were prepared, as described by dissolving 75 g of high-density polysulfone in a liter of DMF. Di-2-ethylhexyl phosphoric acid (DEHPA) was utilized as the metal extractant. One hundred and twenty grams of this liquid extractant was sorbed into 40 g of powdered (minus 100 plus 325 mesh) activated carbon, and the resulting material was blended into the polysulfone-DMF. The activated carbon was added to aid in retention of the DEHPA and not as a metal extractant. The mixture was injected into water, and 50 mL of the resulting beads were contacted in a stirred reactor with 200 mL of a pH 5.0 simulated zinc processing solution containing 1.0 g/L Zn. After 2 hours of contact, the beads were removed from the zinc solution, washed with water, and contacted with 200mL of 100 g/L $H_2SO_4$ for 2 hours. The purpose of the sulfuric acid contact was to strip the zinc values from the loaded beads. After stripping, the beads were rinsed with water and contacted with a fresh aliquot of the zinc processing solution. A total of three loading-stripping cycles were conducted, and the average extraction of zinc from the processing solution was 95.7 percent. Substantially all of the zinc was stripped from the loaded beads by the sulfuric acid solution.

EXAMPLE 4

Polysulfone beads were prepared as described above and in Example 3. The finished beads contained a mixture of two solvent extraction reagents, DEHPA and Cyanex 272. The bead composition was 120 g polysulfone, 22 g DEHPA, 22g Cyanex 272, and 56 g activated carbon per liter of DMF. The beads (25 mL) were contacted in a stirred reactor with 500 mL of waste water draining from an inactive open-pit uranium mining operation. The pH 4.2 waste water contained 5 mg/L Zn and 30 mg/L U. In 2 hours of contact, the zinc content of the waste water was reduced to <1 mg/L, and uranium content was reduced to <4 mg/L.

Beads containing a mixture of DEHPA and an algal biomass (Ulva sp.) were also prepared using the above described procedures. The finished beads contained 100 g polysulfone, 100 g Ulva, 40 g DEHPA, and 60 g activated carbon per liter of DMF. Ten milliliters of the beads were contacted in a stirred reactor with 200 mL of a pH3.8 Zn waste water for 4 hours. The waste water contained 7.8 mg/L Zn and 4.2 mg/L Mn. After 4 hours, 89.5 percent of the zinc and 89.1 percent of the manganese had been sorbed, resulting in an effluent containing <1.0 mg/L Zn and Mn.

This test demonstrates that mixtures of extractants, including microorganisms and chemical compounds, can be utilized in a single bead matrix.

EXAMPLE 5

In order to simulate a chemical precipitation procedure, sodium hypochlorite and caustic was added to waste water draining an inactive zinc operation. The resulting pH 8.0 precipitation effluent contained 14.5 mg/L Zn (a zinc level well above established discharge limits). Polysulfone beads containing 100g polysulfone, 120 g DEHPA as the metal extractant, and 40 g activated carbon per liter of DMF were contacted with the precipitation effluent in a stirred reactor for 2 hours. As in Example 3, the beads were washed with water, contacted with 100 g/L $H_2SO_4$ for 2 hours, and recontacted with a fresh aliquot of waste water for a total of three loading-stripping cycles. An average of 96.3 percent of the zinc was removed from the precipitation effluent for the three cycles, and the bead-treated effluent met established discharge limits.

This example demonstrates that the beads can be utilized as a secondary or "polishing" technique in situations where discharge limits are difficult to achieve using chemical precipitation alone.

EXAMPLE 6

Beads containing 150 g polysulfone and 98 g duckweed (Lemna.sp.) per liter of DMF were prepared as above. The beads were contacted in a fluidized bed, countercurrent column system at a flow rate of 35 BV/h for 24 hours with a zinc waste water. The pH 3.8 waste water contained 7.6 mg/L Zn. After the beads were loaded, they were eluted (or stripped) of zinc. Elution was accomplished using a 0.05M nitric acid solution in the upflow column circuit for 24 hours at a flow rate of 45 BV./h. The eluted beads were then contacted with additional waste water. A total of 16 loading-elution cycles were completed. During the test, the same stripping solution was used for each elution cycle; thus, the zinc concentration in the solution increased proportionally. An average of 86.3 percent of the zinc was extracted for the 16 cycles, and an eluate containing 13.8 times as much zinc as the feed solution was obtained.

This example demonstrates that valuable metal contaminants, such as zinc, can be removed from waste waters using immobilized extractants and concentrated in solutions amenable to further processing.

EXAMPLE 7

Beads containing 150 g polysulfone, 160 g DEHPA, and 200 g activated carbon per liter of DMF were prepared as described above. Fifty milliliters of the beads were contacted with a 1.0 g/L simulated zinc processing solution in a stirred reactor for 2 hours. The loaded beads were washed with water and contacted with 200mL of 100 g/L $H_2SO_4$ for 2 hours. After the beads were rinsed with water, they were contacted with a fresh aliquot of the zinc processing solution. This procedure was repeated for 70 loading-elution cycles. Metal extraction and stripping efficiencies remained constant throughout the 70 cycles, and no physical deterioration of the beads was observed. In addition, liquid chromatography was utilized to determine the loss of DEHPA from the beads into the aqueous streams. Analysis indicated that <2.0 percent of the DEHPA was lost from the beads during the 70 cycles.

Long-term stability tests were also conducted with beads containing 100 g polysulfone and 43 g duckweed (Lemna sp.) per liter of DMF. The beads were contacted with a zinc waste water using an aqueous-to-biomass ratio of 50:1. The pH 3.8 waste water contained 7.6 mg/L Zn and 4.2 mg/L Mn. After.the extraction cycle, the beads were rinsed with water and eluted with 0.2M nitric acid at an aqueous-to-biomass ratio of 50:1 for 0.5 hour. After rinsing, the beads were contacted with additional waste water. These procedures were repeated for a total of 40 loading-elution cycles. Again, no loss in metal extraction efficiency was observed, and no physical deterioration of the beads was noted. These tests demonstrate the excellent chemical and physical stability of these polysulfone beads containing immobilized extractants.

Although polysulfone has been used in the above examples, it is to be understood that other polymeric materials can also be employed to prepare the immobilized extractant beads, as shown in Example 8.

EXAMPLE 8

Beads containing cellulose acetate were prepared by substituting cellulose acetate for polysulfone. The resulting beads contained 100 g cellulose acetate, 50 g DEPHA, and 100 g activated carbon per liter of DMF. Fifty milliliters of the beads were contacted with 100mL of a simulated 1.0 g/L Zn processing solution in a stirred reactor for 2 hours. After 2 hours of contact, the beads were washed with water, stripped of zinc with 100 mL of 100 g/L $H_2SO_4$ and contacted with a fresh aliquot of zinc processing solution. A total of three loading-stripping cycles were conducted, and the average zinc extraction was 99 percent. Thus, substantially all of the zinc was stripped from the loaded beads.

It is apparent that beads containing immobilized extractants effectively removed metal contaminants from very dilute solutions; that the process is not reagent and energy requirement intensive; and, that metal values can be recovered in solutions amenable to further concentration.

Moreover, the biomass and chemical extractants utilized in this invention are immobilized in a porous matrix with an symmetric membrane surface, a loss of extractant during the use of the beads is minimal. The spherical nature of the beads allows considerable flexibility in the choice of processing equipment and easy separation of the beads from aqueous waste streams or processing solutions. Removal of metal values from the extractants is easily accomplished using dilute mineral acids or other dilute solutions. Further, unlike granules containing immobilized extractants, the polysulfone beads have an elastic quality, and are not subject to fracture of attrition; and their excellent handling characteristics are maintained throughout repeated loading-elution cycles.

It has been found that the advantages of the invention over prior metal removal technologies are as follows:

A) The metal extractants are immobilized in a spherical, porous, durable matrix; spherical beads permit easy handling and optimize the surface area available for metal sorption. Spherical beads also allow the use of high-solution flow rates;

B) The beads are not subject to fracture or attrition, and they are stable in strong acid and base solutions;

C) Mixed extractants can be immobilized in the beads when complex waste waters or processing solutions are encountered. Biomass can be blended with chemical extractants in a single bead matrix or combined with other biomass. Likewise, two or more chemical substances can be immobilized in a bead matrix;

D) The addition of activated carbon to the beads containing liquid chemical extractants significantly reduces the loss of the extractants to the aqueous processing streams;

E) The bead matrix containing the immobilized extractants is easily fabricated, and beads with a wide range of physical characteristics can be prepared. For example, beads with densities less than or greater than that of water can be produced, and magnetic beads can be produced to facilitate liquid-solid separations.

While the invention has been described with reference to particular examples, it is to be understood that the examples are illustrative and non-limiting, and that many change can be made without departing from the invention scope, which is defined by the appended claims.

What is claimed is:

1. Water-insoluble spherical beads consisting essentially of polysulfone having an internal pore structure which contains an immobilized synthetic chemical compound extractant sorbed into powdered activated carbon, said synthetic chemical compound extractant and powdered activated carbon being immobilized within the polysulfone and said synthetic chemical compound extractant being capable of sorbing dissolved metals having concentrations less than 1 mg/L in dilute aqueous solutions.

2. Water-insoluble spherical beads according to claim 1, wherein said synthetic chemical compound extractant comprises a mixture of synthetic chemical compound extractants.

3. Water-insoluble spherical beads according to claim 1, wherein said synthetic chemical compound extractant comprises 10% to 68% by weight of said bead.

4. Water-insoluble spherical beads according to claim 1, wherein said synthetic chemical compound extractant is selected from the group consisting of triisooctyl amine, di-2-ethylhexyl phosphoric acid, trioctyl methylammonium chloride, 2-hydroxyl-5-dodecylbenzophenone oxime and di-2-4,4-trimethylpentyl phosphinic acid.

5. A process for making water-insoluble spherical beads consisting essentially of polysulfone having an internal pore structure which contains an immobilized synthetic chemical compound extractant sorbed into powdered activated carbon, said synthetic chemical compound extractant being capable of sorbing dissolved metals having concentrations less than 1 mg/L in dilute aqueous solutions, said method comprising the steps of:
   a) dissolving said polysulfone in an organic solvent;
   b) sorbing a synthetic chemical compound extractant into powdered activated carbon;
   c) blending said synthetic chemical extractant sorbed into powdered activated carbon into the polysulfone organic solvent solution; and
   d) injecting said solution through a nozzle into water to form beads.

6. The process of claim 5, wherein said synthetic chemical compound extractant comprises a mixture of synthetic chemical compound extractants.

7. The process of claim 5, wherein said synthetic chemical compound extractant comprises 10% to 68% by weight of said bead.

8. The process of claim 5, wherein said synthetic chemical compound extractant is selected from the group consisting of triisooctyl amine, di-2-ethylhexyl phosphoric acid, tri-octyl methylammonium chloride, 2-hydroxy-5-dodecylbenzophenone oxime and di-2-4,4-trimethylpentyl phosphinic acid.

9. A method of removing metal contaminants having concentrations less than 1 mg/L in dilute aqueous solutions, said method comprising
   contacting the aqueous solutions with a matrix of water insoluble polymeric beads consisting essentially of polysulfone having an internal pore structure which contains an immobilized synthetic chemical compound extractant sorbed into powdered activated carbon; and
   sorbing said contaminants into said beads.

10. The method of claim 9 wherein said synthetic chemical compound extractant comprises a mixture of synthetic chemical compound extractants.

11. The method of claim 9, wherein said synthetic chemical compound extractant comprises 10% to 68% by weight of said bead.

12. The method of claim 9, wherein said synthetic chemical compound extractant is selected from the group consisting of triisooctyl amine, di-2-ethylhexyl phosphoric acid, tri-octyl methylammonium chloride, 2-hydroxy-5-dodecylbenzophenone oxime and di-2-4,4-trimethylpentyl phosphinic acid.

* * * * *